US011231348B2

(12) United States Patent
Visinoni et al.

(10) Patent No.: US 11,231,348 B2
(45) Date of Patent: Jan. 25, 2022

(54) HISTOLOGICAL SPECIMENS TRACEABILITY APPARATUS AND METHOD

(71) Applicant: Milestone S.r.l., Sorisole (IT)

(72) Inventors: Francesco Visinoni, Mozzo (IT); Matteo Minuti, Brignano Gera d'Adda (IT)

(73) Assignee: MILESTONE s.r.l., Sorisole (IT)

( * ) Notice: Subject to any disclaimer, the term of this patent is extended or adjusted under 35 U.S.C. 154(b) by 339 days.

(21) Appl. No.: 16/260,639

(22) Filed: Jan. 29, 2019

(65) Prior Publication Data

US 2019/0316994 A1 Oct. 17, 2019

(30) Foreign Application Priority Data

Apr. 16, 2018 (EP) .................................... 18167440

(51) Int. Cl.
*G01N 1/31* (2006.01)
*A61B 10/00* (2006.01)
*G01N 1/36* (2006.01)
*G01N 35/00* (2006.01)

(52) U.S. Cl.
CPC .......... *G01N 1/312* (2013.01); *A61B 10/0096* (2013.01); *G01N 1/36* (2013.01); *G01N 2035/00861* (2013.01)

(58) Field of Classification Search
CPC ...... A61B 10/0096; G01N 1/312; G01N 1/36; G01N 2035/00138; G01N 2035/00861; G01N 35/00722; G01N 35/00732
See application file for complete search history.

(56) References Cited

U.S. PATENT DOCUMENTS

| | | |
|---|---|---|
| 5,963,368 A | 10/1999 | Domanik et al. |
| 6,495,106 B1 | 12/2002 | Kalra et al. |
| 10,109,376 B2 | 10/2018 | Visinoni et al. |
| 2005/0186114 A1 | 8/2005 | Reinhardt et al. |
| 2008/0235055 A1 | 9/2008 | Mattingly et al. |
| 2010/0088116 A1 | 4/2010 | Eisenberg et al. |
| 2012/0118954 A1 | 5/2012 | Hagen et al. |
| 2017/0293719 A1 | 10/2017 | Roig Munill et al. |

*Primary Examiner* — Blaine Lankford
(74) *Attorney, Agent, or Firm* — The H.T. Than Law Group

(57) ABSTRACT

The present invention refers to an apparatus (100) for identification of tissue carriers (210) of human or animal tissue that are grouped in a batch (200), wherein the apparatus (100) comprises a working area (110) for receiving the batch (200) of at least two tissue carriers (210); a presence sensor (120) for detecting the presence of each of the tissue carriers (210) of the batch (200) received at the working area (110); an identification device (130) for detecting a unique identifier (220) of each of the tissue carriers (210) of the batch (200) received at the working area (110); and a control unit (140, 141, 142) being configured to identify positions of the working area (110), at which a tissue carrier (210) is detected to be present but no unique identifier (220) is detected and/or at which a unique identifier (220) is detected but no tissue carrier (210) is detected to be present, as identified positions. The present invention further refers to a system (300) as well as a method for tracking and identification of tissue carriers (210) of human or animal tissue.

17 Claims, 3 Drawing Sheets

HISTOLOGICAL SPECIMENS TRACEABILITY APPARATUS AND METHOD

FIELD OF THE INVENTION

Figure 1:
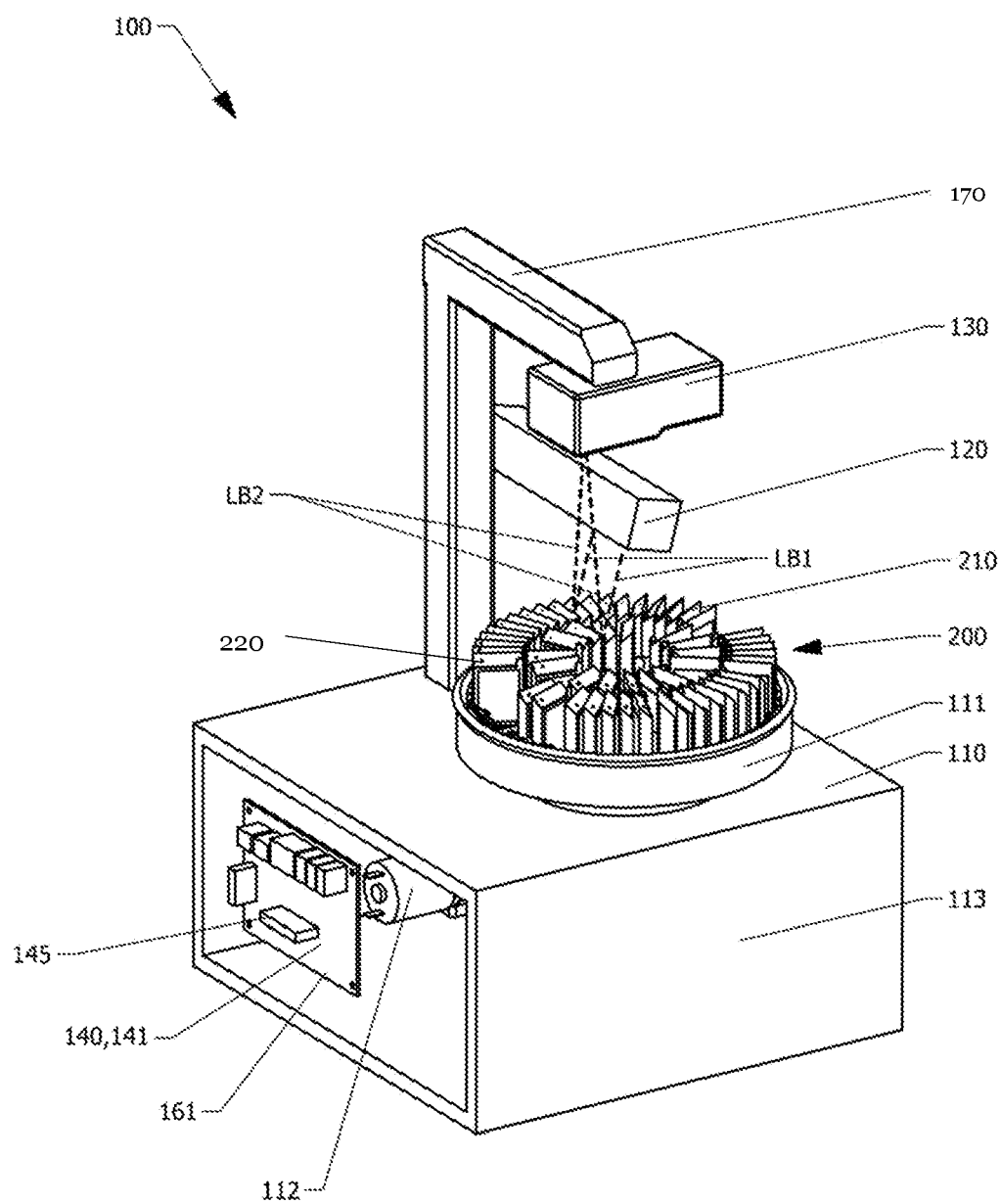

The present invention relates to an apparatus and a system for identification of tissue carriers of human or animal tissue and to a method for tracking and identification of tissue carriers of human or animal tissue.

TECHNICAL BACKGROUND

Usually, tissue specimens or tissue samples are taken at hospital and subsequently transferred to a laboratory or the like for histological examination. For a histological examination of human and/or animal tissue specimens, the tissue specimens are collected from the patients by a clinician in an ambulatory environment (biopsies) or by surgeons during a surgery. After that, the tissue specimens are placed in suitable transportation carriers such as a container. The transportation carrier is typically filled with a fixative such as formalin and sent to the histology laboratory for final examination.

After the histology laboratory has received the tissue specimens, the first operation performed by a histotechnician is the accessioning and grossing.

The accessioning consists of a registration of the incoming tissues and insertion of the data in the Laboratory Information System (LIS). In this phase, a unique tissue code is assigned to the tissue specimen. More specifically, tissue specimens are received, sorted, labeled, e.g. with a barcode label on a carrier such as a container or a histological cassette, in which the tissue specimens are already received and/or in which the tissue specimens will be placed, and related data is entered into the Laboratory Information System (LIS). The data includes, e.g. patient name, required examination, type of the tissue specimen (e.g. organ name), number and/or size of the tissue specimens.

During the following grossing step, the tissue specimen is removed from the original carrier, e.g. a transportation carrier, and reduced in a way that is suitable for the next processes. The reduced tissue specimen is subsequently placed inside a new tissue carrier. The reduced tissue specimen must be small enough to be contained inside this tissue carrier, which is, e.g. a standard (histological) tissue cassette. Some tissue specimens, e.g. small biopsies, are usually already small enough so that the reduction is not required.

Each tissue carrier is usually provided with a unique one-dimensional code (e.g. barcode) or two-dimensional code (e.g. datamatrix). The code is usually printed directly on the surface of the tissue carrier. After the preparation, the tissue carrier is usually grouped together with several other tissue carriers inside a rack or a rack container. A rack may hold from a few tens to a few hundreds of tissue carriers. The rack is then used to process several tissue carriers together at the same time inside a tissue processor. The group of several tissue carriers inside one or more racks is usually named a "batch".

In a next step, processing of the tissue specimens is started. Therefore, the rack is provided in a corresponding tissue processor where—in a first step—the tissue specimens are fixed by use of a fixative solution (e.g. formalin). In a second step, the tissue specimens are dehydrated by use of dehydration reagents (e.g. ethanol). In a third step, the tissue specimens are cleared by use of a clearing reagent (e.g. isopropyl alcohol or xylene). In a fourth step, the tissue specimens are impregnated (or infiltrated) by use of paraffin wax.

The embedding—which is not commonly considered part of the processing and is an operation usually done outside of the tissue processor—is usually done manually or, less commonly, with an automated embedder. The embedding step is required to completely fill the tissue carrier and the impregnated tissue specimen with paraffin wax, creating a solid block. Afterwards, the block is cut and the slides are prepared and finally put under a microscope for a corresponding analysis.

In summary, a high number of the previously described steps exists that are manual steps. Thus, these steps are particularly prone to human error, such as accidentally swapping two samples or accidentally leaving samples behind. Hence, these manual steps are particularly critical for the reliability and traceability of the whole diagnosis process.

In particular, it appears that there is an increasing need for an improvement of the reliability and of the traceability of the diagnosis process during, before and/or after the following manual steps:

a) the step of grouping tissue carriers inside a rack forming a batch;

b) the step of moving the rack from/to the tissue processor.

Step a) of grouping tissue carriers inside a rack forming a batch is critical for knowing which carriers and tissues are processed together in the same tissue processor. By merely assuming the integrity of the group of tissue carriers, it is possible that wrong documentation, which for example is generated by taking the process parameters from a tissue processor for the entire batch, is linked to such tissue carriers of the batch that actually have not been placed in the tissue processor.

Step b) of moving the rack from/to the tissue processor is critical because usually the tissue processor is not close to the area where the tissue carriers are grouped together inside a rack forming a batch. Moreover, filled racks are often not moved to the tissue processor immediately after the preparation. Instead, there is usually a wait time due to the scheduled workflow of the laboratory, during which the filled racks remain unattended. It is possible that an adverse event can happen to the racks during the waiting time or on the transfer route, such as that some tissue carriers fall down from the rack during the movement of the racks from/to the tissue processor or, in case the racks are still left at their place of loading, the racks are accidentally hit, mixed up or misplaced during the waiting time. Thereby, it is for example possible that the loss of certain tissue carriers remains unnoticed until all processing steps for the tissues have been completed. Moreover, the tissue carriers might be processed in a way that was not intended, which would lead to the corruption of the tissue sample.

Hence, it can be summarized that it is particularly important to provide an apparatus and a method for identifying tissue carriers and determining the batch, to which these tissue carriers belong, preferably at a time immediately after preparation of the batch;

checking the consistency, completeness and integrity of a batch at different times and in different places during the process.

In the prior art, tissue carrier tracking control is carried out with one-dimensional code (e.g. a barcode) or two-dimensional code (e.g. datamatrix). Such code is usually printed directly on the surface of the tissue carrier or, less commonly, printed on an adhesive label that is stuck on the tissue carrier. Then the operator usually reads said codes using a handheld optical reader, such as a barcode scanner. The code reading of tissue carriers is done independently for each single tissue carrier in order to identify the single tissue carriers.

However, this method of manually reading a single code at a time is not a particularly suitable and reliable approach for defining or identifying a batch of tissue carriers.

For example, the above mentioned method of the prior art requires in practical terms that the operator reads a great number of codes of tissue carriers one-by-one using a handheld device (a batch usually consists of up to 300 tissue carriers) in order to identify all tissue carriers of a batch. Hence, the time required to manually scan up to 300 tissue carriers with several single code readings (one or two seconds for each single code) is generally considered unaffordable.

Moreover, when the tissue carriers are grouped together inside a rack, the distance between each individual tissue carrier is very small. For this reason, there is an increased risk that the operator misses to scan some of the tissue carriers, for example, by confusing the tissue carrier that was intended for scanning with the tissue carrier preceding or following the one that was intended to be scanned. Hence, it can be concluded that the reliability of the identification and determination of the contents of a batch cannot be guaranteed with such methods of the prior art.

EP 3 200 118 A1 discloses a device and method for traceability of histological samples, comprising a camera that takes a picture of a plurality of tissue carriers, an image processing device that detects and simultaneously reads all the codes of the tissue carriers of said picture, and a screen that shows the picture taken and the information related to the read codes. This document, however, does not disclose a technical solution to verify and certify that the codes of all tissue carriers have been read.

Instead, according to EP 3 200 118 A1, only the readable and detectable codes are displayed. There is no control of tissue carriers with unreadable or missed code. However, in a real scenario, it can happen quite often that an optical code of a tissue carrier is not readable, for example because the code is not well printed, or the code is covered by drops of liquid or blood, or the code is partially hidden by the shadow of other tissue carriers, etc.

It is, however, important to inform the operator even about the tissue carriers with unreadable code, to make the operator able to manage this event properly. Without the detection and recognition of such events it is not possible to guarantee the detection of all tissue carriers that belong to a specific batch.

Milestone's Patent Application EP 16 205 706.1 further describes a method and a system for tracking human and/or animal tissue specimens. However, this document describes a method and a system for a one-by-one detection of tissue carriers being put inside a rack forming a batch, not a method for a bulk identification of all the tissue carriers of a rack or batch at the same time.

It is thus now an object of the present invention to provide an apparatus and a method, which can overcome the aforementioned drawbacks. Moreover, it is a particular object of the present invention to provide a corresponding apparatus, system and method that allows bulk identification of the tissue carriers that are part of the same batch, immediately after the preparation of the batch. In addition, it is an object of the present invention to provide an apparatus, system and a method, which allows to detect tissue carriers with unreadable or missed code, which are part of the batch. Also, it is an object of the present invention to provide an apparatus, system and method, which allow the tracking of the batch and respective tissues during the entire process, in which the batch is involved. Moreover, said apparatus, system and method are intended to facilitate to check the consistency and integrity of the batch onwards from the time the batch is created, i.e. during the grossing step, to the time the batch is disassembled, i.e. immediately before or immediately after the embedding step.

The aforementioned objectives are solved by the subject-matter of the independent claims. The dependent claims define the central idea of the present invention in a particularly advantageous way.

According to a first aspect, the present invention relates to an apparatus for identification of tissue carriers of human or animal tissue that are grouped in a batch.

According to the present invention, "identification of tissue carriers" can generally be understood as establishing and determining distinctive characteristics and features of each of the tissue carriers that allow to differentiate an individual tissue carrier from other tissue carriers. Furthermore, according to the present invention, the term "batch" is generally referred to a group of several (at least two) tissue carriers that are processed together.

The apparatus comprises a working area for receiving the batch of at least two tissue carriers. According to the present invention, the term "working area" is generally to be understood as a (defined) space that is suitable for receiving the batch of tissue carriers.

The apparatus further comprises a presence sensor for detecting the presence of each of the tissue carriers of the batch received at the working area.

According to the present invention, the term "presence of a tissue carrier" can be understood as the physical existence of a tissue carrier within a (defined) space, such as, for example the working area.

Moreover, the apparatus also comprises an identification device for detecting a unique identifier of each of the tissue carriers of the batch received at the working area.

According to the present invention, the term "unique identifier" is a distinctive characteristic or feature of a tissue carrier that sets an individual tissue carrier apart from other tissue carriers.

In addition, the apparatus also comprises a control unit that is configured to identify positions of the working area, at which a tissue carrier is detected to be present but no unique identifier is detected and/or at which a unique identifier is detected but no tissue carrier is detected to be present. These particular positions of the working area are referred to as "identified positions".

In other words, the present invention relates to an apparatus that provides the capability to sense, if tissue carriers are (physically) present within a defined (confined) space. Moreover, the apparatus also provides the capability to distinguish between individual elements of the batch that are placed within the defined (confined) space by detecting and registering their unique identifiers.

The control unit of the present invention utilises these capabilities in order to determine and to locate every tissue carrier of the batch within the defined (confined) space that is either found to be present but not to be distinguishable, or that is found to be distinguishable but not to be present.

For example, such a situation may arise in case the barcode of a tissue carrier that is placed on the working area is covered by a blood stain and thereby the barcode is not be readable. However, the respective tissue carrier is still present at the working area. Alternatively, it is possible that the printed barcode label of a tissue carrier has fallen off and remained on the working area while the tissue carrier itself has been removed. Hence, it is possible that this barcode label is detected on the working area, thereby suggesting the existence of a tissue carrier that does not (physically) exist on the working area. With the solutions described in the prior art, it is not detected that corrupted data is generated and consequently, the data referring to the batch, such as the documentation, will be corrupted.

However, with the apparatus of present invention it is possible to detect and to single out the tissue carriers of the batch, for which inconsistent sensory data exists.

Moreover, it is not only possible to detect such cases, but also to locate the position of such tissue carriers on the working area. Consequently, it is very easy for the operator of the apparatus to gain and to maintain certainty about the configuration by simply checking the respective identified position(s). According to the present invention the term "configuration" relates to the composition or the batch's individual elements, i.e. tissue carriers, of the batch.

Furthermore, with the apparatus of present invention it is possible to overcome the drawback of the prior art of having to complete a high number of steps in time expensive and error prone manual labour, such as the aforementioned identification of the tissue carriers through one-by-one scanning. Instead, the apparatus allows to identify every tissue carrier included in the batch without manual labour. In addition, the capability of the apparatus to validate acquired sensory data guarantees the integrity of the information (data) about the configuration of the batch. This is an essential step in order to generate valid documentation about the processing of the tissue carriers included in the batch.

Moreover, the apparatus of the present invention is not constrained to be used only during certain steps of the process. Instead, the apparatus can be used to validate the configuration of the batch at different locations of the laboratory and during various steps of the tissue processing.

Moreover, in a preferred embodiment of the present invention, the working area comprises defined positions each for receiving only one of the tissue carriers of the batch.

In other words, according to this preferred embodiment of the present invention, the apparatus comprises a working area for receiving the batch of at least two tissue carriers, wherein the working area comprises defined positions each for receiving only one of the tissue carriers of the batch.

According to the present invention, the term "defined position" is to be understood as any position within/on/at/in the working area that is defined by placing a single tissue carrier on the working area. A tissue carrier, for example, is not placed in a "defined position", if it overlaps with another tissue carrier that has already been placed on the working area.

Preferably, the working area comprises a rack that comprises the defined positions. In other words, according to this preferred embodiment, the working area is a rack (compartment/container), in which the tissue carriers of the batch can be placed on defined positions.

Thereby, it is possible to use different types of holders for receiving the tissue carriers, in particular such holders that are commonly used in the processing of tissue. Hence, it is not required to provide a particular enclosure for receiving the batch.

Moreover, the rack can be moveable. Also, the working area, preferably the defined positions and more preferred the rack with the defined positions, can be relatively moveable, preferably rotatable, with respect to the presence sensor and the identification device for the purpose of detecting the presence of the tissue carriers and the unique identifiers, respectively. Therein, the apparatus preferably further comprises a drive unit for the relative movement, wherein the drive unit is further preferably controlled by the control unit.

The provision of a moveable working area on the apparatus allows to further automate the detection of the presence of the tissue carriers placed on the working area as well as detecting their corresponding unique identifiers. Moreover, with this design it can be avoided that tissue carriers are not detected due to the tissue carriers being placed outside a detection zone of the identification device or the presence sensor. Hence, thereby it can be assured that the apparatus acquires all tissue containers of the batch that have been placed on the working area.

According to a further preferred embodiment of the present invention, the control unit and the presence sensor are configured to determine positions of the working area, at which tissue carriers of the batch are detected to be present. These positions are referred to in the following as "presence positions". Alternatively, it is also possible that only one of the control unit and the presence sensor is configured to determine the presence positions.

Also, the control unit and the identification device can be configured to determine positions of the working area, at which unique identifiers of tissue carriers of the batch are detected. These positions are referred to in the following as "ID positions". Alternatively, it is also possible that only one of the control unit and the identification device is configured to determine the ID positions.

Moreover, the control unit is preferably also configured to determine positions of the working area, at which, respectively, exactly one unique identifier of a tissue carrier is detected and at which also exactly one tissue carrier is detected to be present. These positions are referred to in the following as "confirmed positions".

In other words: according to these preferred embodiments, the location of a tissue carrier placed on the working area, and in particular the defined positions of the working area, can be either determined by the control unit or by one of the two sensory units, i.e. identification device or presence sensor. Alternatively, it is also possible that the control unit and one of the sensory units or the control unit together with both of the sensory units are each configured to determine positions of tissue carriers that have been placed on the (defined positions of the) working area.

Thereby, it is possible to acquire information about the location (defined position) of the tissue carrier on the working area besides acquiring sensory data about the presence and/or about the unique identifier of the respective tissue carrier. This information about the location of the respective tissue carrier can be used to point the operator of the apparatus to a location (defined position), for which a mismatch between sensory data of the batch has been determined.

According to a further preferred embodiment of the present invention, the control unit comprises a storage unit for storing data acquired by the presence sensor and the identification device, preferably in a retrievable manner, such as a data base.

Thereby, it is possible to store the acquired data in a manner that allows to utilise the data for a later evaluation. For example, the data can then be used to be integrated into the Laboratory Information System (LIS).

Moreover, it is also conceivable that the apparatus further preferably comprises a venting system to extract exhaust fumes coming from the tissue carriers. Therein, the tissue carriers are preferably received at the defined positions of the working area, preferably of the rack.

Thereby, it is possible to provide the apparatus with the capability to remove and to guide toxic fumes from the apparatus to an air filter. Consequently, the apparatus can be used for a large variety of experiments and processes as well as the apparatus contributes to the well-being and safety of the operators.

Moreover, the control unit preferably comprises an interface unit, such as wired or wireless data exchange unit, for providing external access to the data for external devices and/or for exchange of data with external devices.

Thereby, it is possible to connect the apparatus to a communications network, such as the internet. Hence, it is possible to facilitate the exchange of data between the apparatus and other devices, which can be internal (intra device communication) or external devices (inter device communication) in relation to the apparatus. It is also conceivable to operate the apparatus remotely via the interface unit.

According to a further preferred embodiment of the present invention, the control unit is configured to store as a result of the identification of the control unit the unique identifiers of each of the tissue carriers being detected to be present at the working area, preferably at the defined positions of the working area, more preferred at the confirmed positions. In addition, the control unit is also preferably configured to store any of the identified positions, the confirmed positions, the presence positions or the ID positions.

According to the present invention, the expression "result of the identification" is generally to be understood as any type and form of data acquired by the apparatus as well as any type and form of data derived from an evaluation or processing of such data.

Preferably, the control unit is further configured to quantify any of the following items individually or in any combination and/or in any arbitrary order:
- the number of tissue carriers being detected to be present at the working area, preferably at the defined positions of the working area, or preferably, in other words, the number of presence positions;
- the number of unique identifiers being detected to be present at the working area, preferably at the defined positions of the working area, or preferably, in other words, the number of ID positions;
- the number of unique identifiers of each of the tissue carriers being detected to be present at the working area, preferably at the defined positions of the working area, or preferably, in other words, the number of confirmed positions;
- the number of identified positions.

Thereby, the evaluation of the acquired data with the control unit is facilitated and simplified. Also, more data for evaluation through the operator is generated that can be used for various purposes, such as the documentation of the process or for the maintenance and improvement of the apparatus.

Moreover, the control unit can be configured to create a report in a digital format comprising any of the acquired data for output in a text format or in a graphic format or both. Also, such reports can also comprise any of the data derived by evaluating the acquired data.

Thereby, it is possible to provide the operator of the apparatus with an illustrative representation of the acquired data. This simplifies the analysis, the evaluation and the assessment of data of the batch and/or of any data that can be used for improving and/or maintaining the apparatus for the operator.

According to a further preferred embodiment of the present invention, the control unit is further configured to assign a unique batch identification to the batch. Alternatively or additionally, the control unit is also configured to link a unique batch identification to the batch. Preferably, the unique batch identification is based on at least one of the unique identifiers of the tissue carriers of the said batch.

According to the present invention, the "unique batch identification" is to be understood as an identifier of the batch that represents the configuration (composition) of the batch.

For example, the unique batch identification can contain information about its configuration, e.g. by forming a (an alphanumerical) numerical value based on the unique identifiers of every tissue carrier of the batch. Alternatively, the unique batch identification can solemnly be a reference or numerical address that relates or points to information about the configuration about the batch information, which is stored in a database.

Thereby, it is possible to encapsulate information about the batch within a smaller data structure, such as the unique batch identification. Consequently, it is possible to reduce the amount of computer operations on the control unit. In addition, by assigning or linking the batch to a unique batch identification a computational model of the physical batch of tissue carriers can be created. Hence, the physical batch can be expressed in numerically defined values in the control unit. Consequently, it is possible to determine and store numerical properties of the batch.

Moreover, the control unit is preferably also configured to link the unique batch identification with the data acquired by the detection of the presence sensor and/or the identification device and/or of the identification of the control unit and/or of any information derived therefrom and to store these linked data as batch information.

By linking acquired data about individual tissue carriers of a batch to the unique batch identification it is possible to store and to track the configuration of the batch (i.e. batch information as batch specific information) in a data management system, such as the aforementioned LIS, without the need of transferring and manipulating the entire data set associated with it. Also, it is possible to associate an individual tissue carrier with its corresponding batch. Thereby, for example, it can be easily determined if a tissue carrier is part of a batch or not by simply comparing the batch identification that is linked to each of the two tissue carriers.

According to a further preferred embodiment of the present invention, the apparatus further comprises an output unit. The output unit can be a display, indicator, lamp or speaker, for outputting, preferably visualizing, of various data. Such data can comprise data acquired by the detection of the presence sensor and/or the identification device, and/or data acquired by the identification of the control unit, and/or any other data acquired, such as the confirmed positions, and/or identified positions, and/or the result of the identification of the control unit and/or the results of quantifying. The results of quantifying can comprise
- the number of tissue carriers being detected to be present at the working area, preferably at the defined positions of the working area, and/or the number of presence positions, and/or
- the number of unique identifiers being detected to be present at the working area, preferably at the defined positions of the working area, more preferred at the confirmed positions, and/or the number of ID positions, and/or the number of the confirmed positions, and/or the number of identified positions.

Moreover, also the report created by the control unit, and/or preferably the unique batch identification that is assigned or linked to the group of tissue carriers of the batch, and/or the batch information can be outputted or visualised by the output unit.

Thereby, it is possible to provide the operator with information about the results of the identification, in particular, with information about the completeness of the batch. Also, information can be made available that there is a potential mismatch between the data acquired regarding the presence of a tissue container (on a defined position) and the data acquired regarding the unique identifier of the tissue container (on this defined position). Thereby, it is possible for the operator to check the batch before processing and, if required, to add or remove a tissue carrier that would otherwise be missing in the batch or been incorrectly added to the batch.

The identification device can be an optical reader, such as a barcode scanner, that is configured to read optical codes, such as a one-dimensional code, a barcode, a two-dimensional code, or a datamatrix. Alternatively, the identification device is a RFID reader that is configured to read electronic codes, such as RFID tags, by means of near field technology.

The presence sensor is preferably a photoelectric sensor or laser sensor or a digital camera. The digital camera is preferably a camera with a pattern recognition algorithm to detect the presence of an object, preferably such as a tissue carrier, on an image.

Alternatively, the presence sensor is preferably configured to detect the presence of an object or the distance between a surface of the object, such as the surface of a tissue carrier, and a reference surface of the presence sensor.

Thereby, it is possible to provide the apparatus with electrical components that are common and widely available, so that the costs for manufacturing and maintenance of the apparatus can be reduced.

According to a second aspect, the present invention relates to a system for tracking and identification of tissue carriers of human or animal tissue that are grouped in a batch. The system comprises at least two of the apparatuses according to the first aspect of the present invention that has been described hereinbefore.

Moreover, in the system of the present invention comprises a system control unit that facilitates that the results of the detection of the presence sensors and/or the identification devices and/or the identification of the control units of each of the apparatuses, respectively, are shared and preferably cross-checked and/or compared by all apparatuses.

Thereby, it is possible to determine and/or to detect any change in the configuration (composition) of a batch based on a comparison of a first set of data that originates from the identification in a first apparatus according to the present invention, with a set of data coming from a different apparatus. Consequently, with the system of the present invention it is possible to detect if the batch still contains the same amount of tissue carriers and if the same tissue carriers, which were determined in a previous identification through an apparatus of the present invention, still form a part of the batch.

In particular, the system control unit can be configured to determine any difference between the results of each of the apparatuses with each of the results referring to the same batch. The results of such determination are in the following referred to as "determined results". Preferably, the system control unit is configured to output the determined results.

Hence, it can be seen that the system according to the present invention is provided with the capability to determine the integrity of the batch by facilitating a cross-examination of different data sets corresponding to the same batch. Thereby, the system offers the functionality of securing reliability of data that corresponds to the batch. Moreover, the system improves the efficiency in tissue processing as missing tissue carriers are recognized and, if missing tissue carriers exist, the operator can be notified. Furthermore, the system facilitates the automated generation of documentation about the tissue processing of the batch.

Furthermore, for example, a batch of tissue carriers has been placed in a first apparatus according to the invention before undergoing treatment in a first process (e.g. in the tissue processor). Then, after completion of the first process, the batch is transported to a second place for a second process (e.g. to the embedding station). However, during the first process or during the transport one of the tissue carriers is lost, damaged or stained in a way that its corresponding unique identifier cannot be detected anymore. By placing the batch in a second (or the same) apparatus according to the present invention and operating thereof, it can be checked before proceeding to the second process if the batch is still intact or if tissue carriers are missing.

Hence, it can be seen that with the system of the present invention the integrity of the batch is evaluated in a cross-examination of different data sets corresponding to the same batch. Thereby, the system secures the reliability and integrity of the data corresponding to the batch, and allows to generate valid documentation about the tissue processing of the batch. Moreover, the operator of the system is informed in case a difference in the configuration of the batch exists. Since the apparatus allows to determine the location, where the mismatch between the data occurred (the identified position), the operator can be guided to the respective location on the working area and take appropriate measures to secure the correctness of the batch.

According to a preferred embodiment, the system control unit comprises a central control unit linked to at least one of the control units. Thereby it is possible to store and to evaluate the data coming from different apparatuses on a central control unit. Alternatively or additionally, the system control unit can comprise at least one of the control units. Thereby, it is not required to provide additional computing and controlling devices and, for example, to store data locally within the walls of the laboratory.

It is also conceivable that the system control unit, preferably the central control unit and/or any one of the control units of the apparatuses, is further configured to determine the batch identification belonging to a unique identifier of one of the tissue carriers of the batch for retrieving the related batch information.

Thereby, it is possible to retrieve information about the batch by solely identifying one element of the associated batch. Also, it is possible to immediately detect the affiliation of a tissue carrier to a batch and thereby, it is possible to compare two tissue carriers regarding their affiliation to a batch.

According to a third aspect, the present invention relates also to a method for tracking and identification of tissue carriers of human or animal tissue, comprising the steps of:

a. Providing at least one apparatus as described hereinbefore;

b. grouping at least two tissue carriers to a batch;

c. placing each of the tissue carriers at (or in one of the defined positions of) the working area, preferably in/on the rack, of the apparatus;
d. detecting the presence of each of the tissue carriers of the batch received at the working area by the presence sensor;
e. detecting unique identifiers of the tissue carriers of the batch received at the working area by the identification device; and
f. identifying the positions of the working area, at which a tissue carrier is detected to be present but no unique identifier is detected and/or at which a unique identifier is detected but no tissue carrier is detected to be present, as identified positions by the control unit.

According to a preferred embodiment of the method of the present invention, the method further comprises any of the following steps or any combination thereof:

assigning and/or linking a unique batch identification to the batch, preferably based on at least one of the unique identifiers of the tissue carriers of the said batch, and/or preferably linking the unique batch identification with the data acquired by the detection of the presence sensor and/or the identification device and/or of the identification of the control unit and/or of any information derived therefrom and preferably storing these linked data as batch information preferably on a storage unit of the control unit;

quantifying by the control unit the number of
tissue carriers being detected to be present at the working area, preferably at the defined positions of the working area, more preferred at the confirmed positions, and even more preferred at the identified positions and/or
the presence positions, and/or
unique identifiers being detected to be present at the working area, preferably at the defined positions of the working area, more preferred at the confirmed positions, and even more preferred at the identified positions and/or
the ID positions, and/or
the confirmed positions, and/or
identified positions and preferably storing of the results thereof on a storage unit of the control unit;
creating a report in a digital format comprising any of the acquired data and/or results of the quantification for output in a text format or in a graphic format or both;
storing data acquired by the presence sensor and the identification device, and/or any results of analysing the data by the control unit preferably in a retrievable manner, on a storage unit of the control unit;
moving, preferably rotating, the working area, preferably the defined positions, more preferred the rack with the defined positions, relatively with respect to the presence sensor and the identification device for the purpose of detecting the presence of the tissue carriers and the unique identifiers, respectively;
outputting, preferably visualizing, data acquired by the detection of the presence sensor and/or the identification device, and/or data acquired by the identification of the control unit, by an output unit;
providing a system as described hereinbefore, and sharing and preferably cross-checking and/or comparing of the results of the detection of the presence sensors and/or the identification devices and/or the identification of the control units of each of the apparatuses, respectively, by all apparatuses via a system control unit;
preferably additionally, determining if there is any difference between the results of each of the apparatuses as determined results via system control unit, e.g. the central control unit and/or any one of the control units of the apparatuses, and preferably outputting the determined results; and/or
preferably determining the batch identification belonging to a unique identifier of a tissue carrier for retrieving the related batch information, preferably via the system control unit, e.g. the central control unit and/or any one of the control units of the apparatuses.

DESCRIPTION OF THE INVENTION

Further advantages and specific features will now be described with respect to the accompanied figures, which show:

FIG. 1 an enlarged perspective view of an apparatus according to an embodiment of the present invention.

Figure 2:
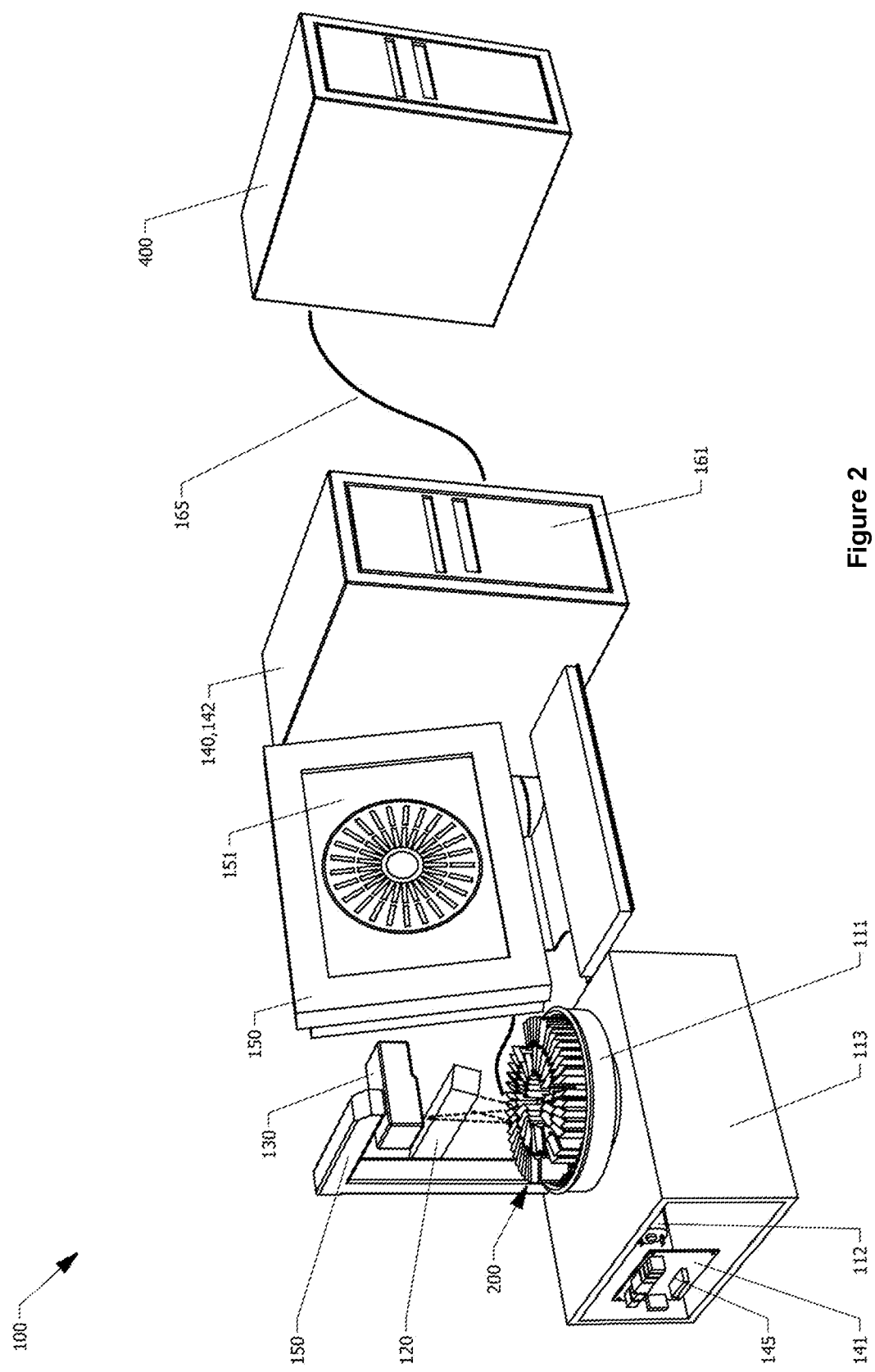

FIG. 2 a perspective view of an apparatus according to a further embodiment of the present invention.

Figure 3:
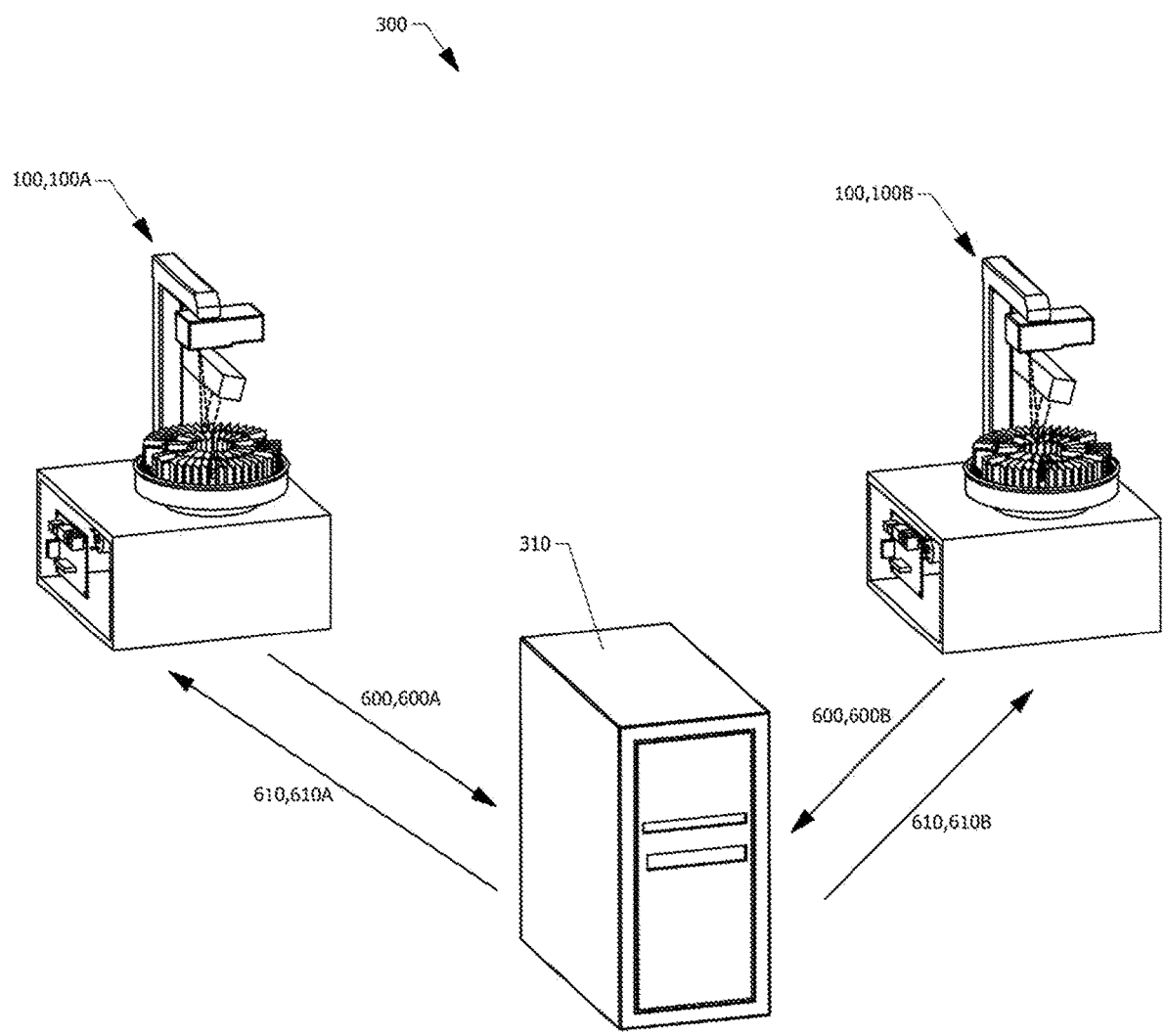

FIG. 3 a schematic view of an embodiment of a system according to the present invention.

Each of FIGS. 1 and 2 shows an embodiment of the apparatus 100 according to the present invention. FIG. 3 shows an embodiment of the system 300 of the present invention comprising two apparatuses 100 of the present invention.

FIG. 1 shows an apparatus 100 for identification of tissue carriers 210 of human or animal tissue that are grouped in a batch 200. The tissue carriers 210, which are suitable for the apparatus 100, can be of different types, sizes and materials. For example, the tissue carrier 210 can be a container or a histological cassette, in which the tissue specimen is received. The tissue carrier 210 can be formed, for example, of a polymer, such as POM.

According to the present invention, the batch 200 consists of at least two tissue carriers 210.

The apparatus 100 comprises a working area 110 for receiving the batch 200. Preferably, the working area 110 comprises defined positions each for receiving only one of the tissue carriers 210 of the batch 200.

The working area 110 can have different sizes and shapes as well as being formed of different materials. For example, the working area 210 can be a round or rectangular plastic or metal tray (not displayed). The tray can have a raised rim to contain the liquid coming from the tissue carriers 210. Moreover, as illustrated in FIGS. 1 and 2 the working area 110 can also be embodied as a rack 111 that comprises the defined positions. The rack 111 can be moveable. Alternatively, the aforementioned tray can have a structure that allows placing of the rack 111 only in a predetermined position.

The apparatus 100 further comprises a presence sensor 120 for detecting the presence of each of the tissue carriers 210 of the batch 200 received at (the defined positions of) the working area 110.

The presence sensor 120 can be a photoelectric sensor, a laser sensor or a digital camera. If a photoelectric sensor is used, it should be considered that the light spot of the photoelectric sensor must be smaller than the gap between two adjacent tissue carriers 210 inside the rack 111, e.g. the light spot has to be less than 3 mm of diameter. The presence sensor 120 can also be a capacitive presence sensor, inductive proximity sensor, proximity switch, ultrasonic distance sensor or the like. Additionally, it is conceivable that the presence sensor 120 can be a camera with a pattern recognition algorithm or a camera connected to a computer that can execute a pattern recognition algorithm. The presence sensor 120 can also be configured to detect the presence of an object by determining the distance between a surface of the object, such as one of the tissue carriers 210, and a reference surface of the presence sensor 120. This optional implementation of the presence sensor 120 is exemplarily illustrated in FIGS. 1 and 2, whereby a first set of dashed lines LB1 is used to indicate the path of a laser beam that runs between the presence sensor 120 and the tissue carriers 210 of the batch 200.

The apparatus 100 further comprises an identification device 130 for detecting a unique identifier 220 of each of the tissue carriers 210 of the batch 200 received at (the defined positions of) the working area 110.

The identification device 130 is preferably configured to transform the unique identifier 220 of the tissue carrier 210 into a corresponding (alphanumerical) numerical value. This numerical value can be further computationally processed.

The unique identifier 220 of each of the tissue carriers 210 can be a barcode or a two-dimensional code or a datamatrix. The unique identifier 220 is preferably printed directly onto the tissue carrier 210. Alternatively, the unique identifier 220 can also be printed on an adhesive label that is applied to the tissue carrier 210. Moreover, it is also conceivable that the unique identifier 220 of the tissue carriers 210 is contained within the shape or the coloring of the tissue carrier 210 itself. However, this enumeration of examples for possible implementations of the unique identifier 220 of the tissue carriers 210 is not delimiting.

In FIG. 1, the unique identifiers 220 of the tissue carriers 210 are provided on the tissue carriers 210. It is also conceivable that each tissue carrier 210 can have more than one unique identifier 220, if required. The position of the unique identifier 220 on the tissue carrier 210 as displayed in FIG. 1 is only an example to illustrate where the unique identifier 220 on the tissue carrier 210 can be placed. Moreover, the unique identifiers 220 are only displayed in FIG. 1 but not in the remaining figures. However, this is only for illustration purposes.

The identification device 130 can be an optical reader, such as a barcode scanner, that is configured to read optical codes, such as a one-dimensional code, a barcode, a two-dimensional code, or a datamatrix. Alternatively, the identification device 130 can be a RFID reader that is configured to read electronic codes, such as RFID tags, by using solutions of near field technology (NFC). The identification device 130 can be configured to scan a specific area of the working area 110 only.

For example, the identification device 130 can be configured to only detect the unique identifiers 220 of the tissue carriers 210 within the area, to which the presence sensor 120 points to. This is exemplarily illustrated in FIGS. 1 and 2, whereby the identification device 130 is resembled by an optical reader and the scanning area of the optical reader is visualized by a second pair of dashed lines LB2.

It is also conceivable that the apparatus 100 is provided with more than one identification device 130 and with more than one presence sensor 120. This configuration is advantageous, for instance, to concurrently analyze the rows of an exemplary rack 11 carrying tissue carriers 210 placed in more than one row, thus it is possible to reduce the time required for scanning and for the subsequent analysis.

The apparatus 100 further comprises a control unit 140 that is configured to identify (the defined) positions of the working area 110, at which a tissue carrier 210 is detected to be present but no unique identifier 220 is detected and/or at which a unique identifier 220 is detected but no tissue carrier 210 is detected to be present, as identified positions. Thereby, it is possible to detect not only a mismatch between the sensory data coming from the presence sensor 120 and the identification device 130, but also to locate the position on the working area 110, where such a mismatch can be found. The importance of this feature will be more apparent from the description provided in the paragraphs further below.

The control unit 140 can be an electronic control board 141, such as displayed in FIG. 1, or a personal computer 142 that uses the input and output ports of the electronic control board 141, as displayed in FIG. 2. Alternatively, different implementations of the control unit 140 are conceivable.

The control unit 140 can be configured to determine presence positions, which are (the defined) positions of the working area 110, at which tissue carriers 210 of the batch 200 are detected to be present.

However, it is also possible that the presence sensor 120 determines the presence positions.

Furthermore, the control unit 140, such as in the example of FIGS. 1 and 2, is preferably also configured to determine ID positions, which are (the defined) positions of the working area 110, at which unique identifiers 220 of tissue carriers 210 of the batch 200 are detected. However, it is also possible that the identification device 130 determines the ID positions.

Moreover, the control unit 140 is also configured to determine confirmed positions, which are (the defined) positions of the working area 110, at which, respectively, exactly one unique identifier 220 of a tissue carrier 210 is detected and at which also exactly one tissue carrier 210 is detected to be present.

The information about the positions of the tissue carriers 210 can be acquired in various ways. For example, the working area 110 or the rack 111 can comprise slots or predetermined openings for receiving the tissue carriers 210. Alternatively, there might be visual reference marks indicating the position on the working area 110 that can be recognized by the presence sensor 120 and/or the identification device 130. Also, it is conceivable that the working area 110 comprises additional sensing devices, such as pressure sensors that allow to determine the position of a tissue carrier 210 on the working area 110. However, this enumeration is not delimiting.

As mentioned before, the rack 111 can be moveable. However, it is also conceivable to provide the working area 110, preferably the defined positions and more preferred the rack 111 with the defined positions, relatively moveable, preferably rotatable, with respect to the presence sensor 120 and the identification device 130 for the purpose of detecting the presence of the tissue carriers 210 and the unique identifiers 220, respectively.

To facilitate the relative movement the apparatus 100 preferably comprises a drive unit 112. Thereby, the drive unit 112 is preferably controlled by the control unit 140.

The drive unit 112 can be composed of at least one motor, preferably a stepper motor, that is able to move the working area 110, preferably the rack 111, in a rotary way around a central axis or, alternatively, in a linear way along one or two axis. In FIGS. 1 and 2 the drive unit 112 is illustrated as a stepper motor that moves the rack 111 around a central axis of the working area 110.

The control unit 140 preferably comprises an interface unit 145, such as a wired or wireless data exchange unit, for providing external access to the data for external devices 400 and/or for exchange of data with external devices 400.

Therefore, as displayed in FIGS. 1 and 2, the electronic control board 141 can be provided with a communication port that facilitates communication via Ethernet, EIA-RS485, EIA-RS422, EIA-RS232 or the like. Alternatively, also the personal computer 142 can be provided with such a communication port.

The control unit 140 can further comprise a storage unit 161 for storing data acquired by the presence sensor 120 and the identification device 130. Preferably the data is stored in a retrievable manner, for example the data can be stored in a data base. The storage unit 161 can be integrated in the control unit 140 such as displayed in FIGS. 1 and 2. The storage unit 161 can be a computer memory, a hard disk or an external hard drive connected to the control unit 140.

The apparatus 100 can further comprise a venting system (not displayed) to extract exhaust fumes coming from the tissue carriers 210. Therein, the tissue carriers 210 are preferably received at the defined positions of the working area 110, preferably of the rack 111. For example, the venting system can be an industrial air filter system such as commonly used in chemical applications.

Moreover, FIGS. 1 and 2 show an exemplary illustration for a mechanical implementation of arranging and connecting the components of the apparatus 100. Therein, the identification device 130 and the presence sensor 120 are mounted to a cantilever 170. The cantilever 170 is preferably mounted to a chassis 113 of the apparatus 100. Also, the control unit 140 as well as the drive unit 112 are preferably connected to the chassis 113.

The control unit 140 is preferably configured to store the unique identifiers 220 of each of the tissue carriers 210 that have been detected to be present at (the defined positions of) the working area 110. Alternatively or additionally, the control unit 140 can be also configured to store the unique identifiers 220 (only for) at the confirmed positions. Moreover, the control unit 140 can also be configured to store any combination or position of the group consisting of the identified positions, the confirmed positions, the presence positions or the ID positions. For example, the so stored data can be seen as the result of the identification of the control unit 140.

Moreover, the control unit 140 is preferably further configured to complete further computation such as conducting a quantification of the stored data. For example, the control unit 140 can be configured to quantify the number of tissue carriers 210 being detected to be present at (the defined positions of) the working area 110. As described before, these positions can also be referred to as presence positions. Alternatively or additionally, the control unit 140 can be configured to quantify the number of unique identifiers 220 being detected to be present at (the defined positions of) the working area 110. As described before, these positions can also be referred to as ID positions. Alternatively or additionally, the control unit 140 can be further configured to quantify the number of unique identifiers 220 of each of the tissue carriers 210 being detected to be present at (the defined positions of) the working area 110. As described before, these positions can also be referred to as confirmed positions. Alternatively or additionally, the control unit 140 can be further configured to quantify the number of identified positions. These (exemplary) data are also referred to as the results of quantifying.

The control unit 140 is further preferably configured to assign and/or link a unique batch identification to the batch 200, preferably based on at least one of the unique identifiers 220 of the tissue carriers 210 of the said batch 200. The control unit 140 is preferably configured to link the unique batch identification with the data acquired by the detection of the presence sensor 120 and/or the identification device 130 and/or of the identification of the control unit 140 and/or of any information derived therefrom and to store these linked data as batch information.

For example, it is conceivable that the unique batch identification mirrors the unique identifiers 220. However, the unique batch identification can also be based on all unique identifiers 220 of the tissue carriers 210 of the batch 200. Moreover, it is also conceivable to use a barcode printed on the rack 111 comprising the batch 200 for the unique batch identification. Thereby, it is possible to associate also the rack 111 with data acquired for the batch 200. Consequently, the different process steps completed with the rack 111 can be tracked and thereby, it is possible to make predictions about the wear and tear of the rack 111 in order to avoid, for example, material fatigue of the rack 111 after the rack 111 being used for an extended period of time.

The control unit 140 can be further configured to create a report in a digital format comprising any of the acquired data for output in a text format or in a graphic format or both.

The apparatus 100 can further comprise an output unit 150 preferably for outputting (visualizing) of any data acquired during the identification process and/or for notifying the operator about faults of the apparatus 100. The output unit 150 can be a display 151 such as illustrated in FIG. 2.

Alternatively or additionally, it is also conceivable to provide the output unit 150 as an indicator, lamp or a speaker. Naturally, this enumeration is not limiting.

The output unit 150 is preferably provided for outputting, preferably visualizing, of data acquired by the detection of the presence sensor 120 and/or the identification device 130. Alternatively or additionally, also data acquired by the identification of the control unit 140 and/or any other data acquired, such as the confirmed positions, and/or identified positions, and/or the result of the identification of the control unit 140 and/or the aforementioned results of quantifying can be outputted. Preferably, also the unique batch identification that is assigned or linked to the group of tissue carriers 210 of the batch 200, and/or the batch information are outputted.

In addition, it is also conceivable that the output unit 150 outputs the report created by the control unit 140. Therein, the report comprises, for example, the number of tissue carriers 210 detected, positions of tissue carriers 210 with respect to the rack 111, number of tissue carriers 210 without a unique identifier 220 (which corresponds, for example, with the difference between the number of presence positions and the number of ID positions), number of tissue carriers 210 with readable unique identifiers 220 (number of ID positions) and the alphanumeric value of such readable unique identifiers 220 of the tissue carriers 210 of the batch 200.

Such displayed report can be a drawing representing the (defined) position of the tissue carriers 210 detected inside the rack ill with the alphanumeric value of the related readable unique identifiers 220 and/or a table showing the number of tissue carriers 210 detected to be present, the number of tissue carriers 210 with missing unique identifiers 220, the number of tissue carriers 210 with readable unique identifiers 220 and the alphanumeric value of such readable unique identifiers 220. The previous described data can be further elaborated by the control unit 140 to display a warning message via the output unit 150 to the user if there are identified positions. This, for example, is displayed on the output unit 150 of FIG. 2, whereby a schematical representation of the rack 111 displays the location of the tissue carriers 210 in relation to the rack 111. The identified positions can be, for example, visualised in a different colour or highlighted in a different manner on such a schematic. Preferably, also the unique batch identification that is assigned or linked to the group of tissue carriers 210 of the batch 200, and/or the batch information are included in the report.

In particular, the control unit 140 displayed in FIG. 2 runs a software application on the personal computer 142. Therein, the personal computer 142 is connected with a display 151 as the output unit 150, for example, via a cable that connects to a correspondingly adapted connection port of the control unit 140. Moreover, the personal computer 142 receives data coming from the electronic control board 141 and generates a report for the user. The personal computer 142 can store the report either locally (for example on the (storage unit 161) memory of the personal computer 142) or it can share the report to other computers over a network, such as LAN (local area network) or WAN (wide area network) or internet, using a (physically) wired or wireless communication line, such as Ethernet or wireless (Wi-Fi) connection. This is exemplarily illustrated by a wire connection 165 in FIG. 2. The personal computer 142 and the display 151 can further comprise Human Interface Devices (HID), such as mouse, keyboard and touchscreen.

FIG. 3 illustrates an embodiment of the system 300 for tracking and identification of tissue carriers 210 of human or animal tissue that are grouped in a batch 200. The system 300 comprises at least two of the apparatuses 100 described hereinbefore. In FIG. 3, this is illustrated by the apparatuses 100A and 100B.

The system 300 comprises a system control unit 310 for sharing and preferably cross-checking and/or comparing of any results of the detection of the presence sensors 120 and/or the identification devices 130 and/or the identification of the control units 140 of each of the apparatuses 100, respectively.

However, with regards to the provision of at least two apparatuses 100 it should be noted that the system 300 does not necessarily require the provision of two (actual) physical apparatuses 100. Alternatively, it is also conceivable that at least one of the apparatuses 100 is simulated via software (virtual apparatus 100), for example by providing an additional control element on the user interface. Thereby, it can be achieved that, despite having only a single apparatus 100 in the laboratory, still a check and validation of the integrity of the configuration of the batch 200 can be completed.

The system control unit 310 preferably comprises a central control unit 310 that is linked to at least one of the control units 140, such as exemplarily illustrated in FIG. 3. For example, a server unit could be used to link the apparatuses 100 of the system 300. Alternatively, it is also conceivable that the system control unit 310 comprises at least one of the control units 140.

The system control unit 310, preferably the central control unit 310 and/or any one of the control units 140 of the apparatuses 100, are configured to determine any difference 610 between the results 600 (results 600 herein generally refer to any data acquired or derived during the acquisition and operation of the apparatus 100) of each of the apparatuses 100 as determined results 610, whereby, preferably, each of the results 600A and 600B refers to the same batch 200.

Preferably, the system 300, in particular the central control unit 310 or the system control unit 310 (or any of the apparatuses 100, or in particular, any of the control units 140 comprised therein) is/are configured to output the determined results 610.

It is exemplarily displayed in FIG. 3 that the system control unit 310 is a central control unit 310, which links the two apparatuses 100A and 100B. Therein, the apparatus 100A shares the results 600A of the identification via the interface unit 145A with the system control unit 310. Also, the apparatus 100B shares the results 600B of the identification via its interface unit 145B with the system control unit 310. Hence, the system 300 facilitates a comparison of the results 600A and 600B with each other and thereby, it is possible to determine if there is any difference 610 between the two data sets, in particular between the results 600A and 600B. The result of this analysis can be sent to each of the apparatuses 100A, 100B as determined results 610A and 610B.

The system control unit 310, preferably the central control unit 310 and/or any one of the control units 140 of the apparatuses 100, is further preferably configured to determine the batch identification belonging to a unique identifier 220 of one of the tissue carriers 210 of the batch 200 for retrieving the related batch information.

In the following paragraph, an exemplary embodiment for the method for tracking and identification of tissue carriers 210 of human or animal tissue according to the present invention is described.

At first, at least one apparatus 100 according to the present invention and exemplarily described hereinbefore is provided. Preferably, the apparatus 100 waits for a rack 111 to be placed in the working area 110 by the user.

Subsequently, at least two tissue carriers 210 are grouped to the batch 200. Each of the tissue carriers 210 is placed at the (defined positions of the) working area 110. Preferably, the tissue carriers 210 are placed in/on the rack 111. For example, once the rack 111 contains several tissue carriers 210 (forming the batch 200) and is placed in the working area 110, the user can start the analysis through a physical button or a virtual button that displayed on the display 151 by the software application that runs on the personal computer 142.

The presence sensor 120 of the apparatus 100 is used for detecting the presence of each of the tissue carriers 210 of the batch 200 received at the (defined positions of the) working area 110. Simultaneously or subsequently, the unique identifiers 220 of the tissue carriers 210 of the batch 200, which are received at the (defined positions of the) working area 110, are detected by the identification device 130.

Moreover, the positions of the working area 110, at which a tissue carrier 210 is detected to be present but no unique identifier 220 is detected and/or at which a unique identifier 220 is detected but no tissue carrier 210 is detected to be present, are identified by the control unit 140 as identified positions.

Preferably, the (defined positions of the) working area 110, preferably the rack 111 with the defined positions, are relatively moved (rotated) with respect to the presence sensor 120 and the identification device 130 for the purpose of detecting the presence of the tissue carriers 210 and the unique identifiers 220, respectively.

For example, for an apparatus as described in FIG. 2, the electronic control board 141 can be configured to activate the drive unit 112. The drive unit 112 then moves the rack 111 in a way that each slot of the rack 111 provided for the tissue carriers 210 passes under the identification device 130 and the presence sensor 120. This can be achieved, for example, by a rotary movement if the rack 111 has the slots arranged in a circular fashion on the rack 111, or by a linear movement, if the rack 1 has its slots arranged linearly in a line. Alternatively, it is also conceivable to combine several rotary and/or linear movements, if the rack 111 has multiple circular or linearly arranged rows of slots. In this particular example, the defined positions are embodied through the slots. This, however, is not limiting but only to be seen as an example. The software running on the control unit 140 can be previously set with the data regarding the geometry of the rack 111 to implement the proper movement. When the rack 111 is moving, the presence sensor 120 detects the presence of the tissue carriers 210 passing under said presence sensor 120. The presence sensor 120 can then be configured to send the presence information to the electronic control board 141.

When the tissue carrier's 210 presence is detected, the electronic control board 141 can be configured to activate the identification device 130 to detect and read a code printed on the tissue carrier 210. The information related to the code of the tissue carrier 210 detected (even comprising the information of unreadable or missed code) can be sent to the personal computer 142 by the electronic control board 141. The movement and the identification process can be stopped when all slots of the rack 111 have been analysed. For example, the execution time of all the steps described above is between 3 to 30 seconds for a rack 111 of seventy tissue carriers if using the apparatus 100 of the present invention. Therefore, it is apparent that the apparatus of the present invention is particularly suited for bulk identification of the batch 200 consisting of a high number of the tissue carriers 210.

Moreover, it is conceivable that a unique batch identification is assigned and/or linked to the batch 200. As stated before, the unique batch identification is preferably based on at least one of the unique identifiers 220 of the tissue carriers 210 of the said batch 200. Furthermore, preferably the unique batch identification is linked with the data acquired by the detection of the presence sensor 120 and/or the identification device 130 and/or of the identification of the control unit 140, and/or of any information derived therefrom. Moreover, preferably these linked data are stored as batch information, preferably on a storage unit 161 of the control unit 140.

For example, the personal computer 142 can automatically assign or link the unique batch identification to the group of the tissue carriers 210 detected. The personal computer 142 can store the result data locally (on the memory of said computer 142) or can share the acquired data with other computers 400 over a network, such as LAN (local area network) or WAN (wide area network) or internet, using a proper communication line, such as Ethernet or wireless (Wi-Fi) connection. The user can also query the computer 142 to get information from the stored data regarding a specific tissue carrier 210, i.e. getting the information about the batch 200, to which said tissue carrier 210 belongs, and getting information about which other tissue carriers 210 belong to the same batch 200. Furthermore, since the data stored is provided in a machine-readable manner, other machines, such as a tissue processor, can also query the computer 142 to get such information.

Also, it is conceivable that the control unit 140 completes a number of quantification calculations, such as quantifying the number of tissue carriers 210 being detected to be present at the defined positions of the working area 110 and/or at the confirmed positions and/or at the identified positions. Similar preferably applies to the quantification of the presence positions, the unique identifiers 220 being detected to be present at the working area 110 and/or present at the confirmed positions and/or present at the identified positions.

Preferably such results 600 or any data acquired by the presence sensor 120 and the identification device 130 are stored on a storage unit 161 of the control unit 140. Preferably, the data is stored in a retrievable manner on a storage unit 161 of the control unit 140. Also, it is conceivable to create a report in a digital format comprising any of the acquired data and/or results of the quantification for output in a text format or in a graphic format or both.

Moreover, the data acquired by the detection of the presence sensor 120 and/or the identification device 130, and/or data acquired by the identification of the control unit 140 is outputted (and/or visualised) by an output unit 140. For example, the computer 142 can also be configured to recall previously stored data and to match such data with other previously stored data or with recently acquired data. The result of this match can then be displayed to the user on the display 151.

In another, preferred embodiment of the method of the present invention, it is conceivable to provide a system 300 according to the invention as described hereinbefore.

Therein, the results 600 of the detection of the presence sensors 120 and/or the identification devices 130 and/or the identification of the control units 140 of each of the apparatuses 100 are shared and/or cross-checked and/or compared respectively, by all apparatuses 100 via a system control unit 310.

For example, the identification of the batch 200 is completed in each of the two different apparatuses 100 of the system 300. Thereby, data is acquired in each of the apparatuses 100 that relates to the same batch 200. The data sets coming from each of the apparatuses 100 can then be shared and compared via a system control unit 310, such as, for example, a server unit.

Moreover, it is also preferable to determine if there is any difference 610 between the results 600 of each of the apparatuses 100 of the system 300. This determination is preferably conducted by the system control unit 310, e.g. the central control unit 310 and/or any one of the control units 140 of the apparatuses 100 and it is referred to the results of such determination as determined results 610. Preferably, the determined results 610 are also outputted.

Moreover, it is also conceivable that the batch identification belonging to a unique identifier 220 of a tissue carrier 210 is determined in order to retrieve the related batch information. Preferably, this is accomplished via the system control unit 310, e.g. the central control unit 310 and/or any one of the control units 140 of the apparatuses 100. For example, the operator can identify the batch 200 very easily by scanning only one tissue carrier 210 that is part of the batch 210, if the batch 200 has already been identified in an earlier step or in a different apparatus 100 of the system 300.

The present invention is not limited to the embodiments as described above. All the features in the embodiments can of course be interchangeably combined as long as being covered by the appended claims. In particular, the layout of the apparatus or the system as well as the order and the number of the steps of the methods are not limited.

The invention claimed is:

1. Apparatus (100) for identification of tissue carriers (210) of human or animal tissue that are grouped in a batch (200), wherein the apparatus (100) comprises:
a working area (110) for receiving the batch (200) of at least two tissue carriers (210);

a presence sensor (120) for detecting the presence of each of the tissue carriers (210) of the batch (200) received at the working area (110);
an identification device (130) for detecting a unique identifier (220) of each of the tissue carriers (210) of the batch (200) received at the working area (110); and
a control unit (140, 141, 142) being configured to identify positions of the working area (110), at which a tissue carrier (210) is detected to be present but no unique identifier (220) is detected and/or at which a unique identifier (220) is detected but no tissue carrier (210) is detected to be present, as identified positions.

2. Apparatus (100) according to claim 1, wherein the working area (110) comprises defined positions each for receiving only one of the tissue carriers (210) of the batch (200), wherein the working area (110) comprises a moveable rack (111) comprising the defined positions.

3. Apparatus (100) according to claim 1, wherein the control unit (140, 141, 142) and/or the presence sensor (120) is configured to determine presence positions, which are positions of the working area (110), at which tissue carriers (210) of the batch (200) are detected to be present, and/or
wherein the control unit (140, 141, 142) and/or the identification device (130) is configured to determine ID positions, which are positions of the working area (110), at which unique identifiers (220) of tissue carriers (210) of the batch (200) are detected, and/or
wherein the control unit (140, 141, 142) is configured to determine confirmed positions, which are positions of the working area (110), at which, respectively, exactly one unique identifier (220) of a tissue carrier (210) is detected and at which also exactly one tissue carrier (210) is detected to be present.

4. Apparatus (100) according to claim 1, wherein the working area (110) is relatively moveable with respect to the presence sensor (120) and the identification device (130) for the purpose of detecting the presence of the tissue carriers (210) and the unique identifiers (220), respectively.

5. Apparatus (100) according to claim 1, wherein the control unit (140, 141, 142) comprises a storage unit (161) for storing data acquired by the presence sensor (120) and the identification device (130) in a retrievable manner.

6. Apparatus (100) according to claim 1, wherein the control unit (140, 141, 142) is configured to store the unique identifiers (220) of each of the tissue carriers (210) being detected to be present at the working area (110) and
wherein the control unit (140, 141, 142) is further configured to quantify
the number of tissue carriers (210) being detected to be present at the working area (110), and/or
the number of unique identifiers (220) being detected to be present at the working area (110), and/or
the number of unique identifiers (220) of each of the tissue carriers (210) being detected to be present at the working area (110), and/or
the number of identified positions.

7. Apparatus (100) according to claim 1, wherein the control unit (140, 141, 142) is configured to create a report in a digital format comprising any of the acquired data for output in a text format or in a graphic format or both.

8. Apparatus (100) according to claim 1, wherein the control unit (140, 141, 142) is further configured to assign and/or link a unique batch identification to the batch (200) based on at least one of the unique identifiers (220) of the tissue carriers (210) of the said batch (200), and
wherein the control unit (140, 141, 142) is configured to link the unique batch identification with the data acquired by the detection of the presence sensor (120) and/or the identification device (130) and/or of the identification of the control unit (140, 141, 142) and/or of any information derived therefrom and to store these linked data as batch information.

9. Apparatus (100) according to claim 1 further comprising an output unit (150) for outputting of data acquired by the detection of the presence sensor (120) and/or the identification device (130), and/or data acquired by the identification of the control unit (140, 141, 142), and/or any other data acquired, comprising the confirmed positions, and/or the identified positions.

10. Apparatus (100) according to claim 1, wherein the identification device (130) is an optical reader that is configured to read optical codes, or wherein the identification device (130) is a RFID reader that is configured to read electronic codes, and/or
wherein the presence sensor (120) is a photoelectric sensor or laser sensor or a digital camera, wherein the presence sensor (120) is configured to detect the presence of an object or the distance between a surface of the object and a reference surface of the presence sensor (120).

11. Apparatus (100) according to claim 1 wherein the apparatus (100) further comprises a venting system to extract exhaust fumes coming from the tissue carriers (210).

12. System (300) for tracking and identification of tissue carriers (210) of human or animal tissue that are grouped in a batch (200), comprising at least two of the apparatuses (100, 100A, 100B) according to claim 1,
wherein results (600, 600A, 600B) of the detection of the presence sensors (120) and/or the identification devices (130) and/or the identification of the control units (140, 141, 142) of each of the apparatuses (100, 100A, 100B), respectively, are shared and cross-checked and/or compared by all apparatuses (100, 100A, 100B) via a system control unit (310).

13. System (300) according to claim 12, wherein the system control unit (310) comprises a central control unit (310) linked to at least one of the control units (140, 141, 142) and/or the system control unit (310) comprises at least one of the control units (140, 141, 142).

14. System (300) according to claim 12, wherein the system control unit (310), and/or any one of the control units (140, 141, 142) of the apparatuses (100, 100A, 100B) are configured to determine any difference (610, 610A, 610B) between the results (600, 600A, 600B) of each of the apparatuses (100, 100A, 100B) with each of the results (600, 600A, 600B) referring to the same batch (200) as determined results (610, 610A, 610B), and is/are configured to output the determined results (610, 610A, 610B).

15. System (300) according to claim 12, wherein the system control unit (310) and/or any one of the control units (140, 141, 142) of the apparatuses (100, 100A, 100B) is further configured to determine a batch identification belonging to a unique identifier (220) of one of the tissue carriers (210) of the batch (200) for retrieving related batch information.

16. Method for tracking and identification of tissue carriers (210) of human or animal tissue, comprising the steps of:
a. providing at least one apparatus (100) according to claim 1;
b. grouping at least two tissue carriers (210) to a batch (200);
c. placing each of the tissue carriers (210) at the working area (110) of the apparatus (100);

d. detecting the presence of each of the tissue carriers (210) of the batch (200) received at the working area (110) by the presence sensor (120);

e. detecting unique identifiers (220) of the tissue carriers (210) of the batch (200) received at the working area (110) by the identification device (130); and f. identifying the positions of the working area (110), at which a tissue carrier (210) is detected to be present but no unique identifier (220) is detected and/or at which a unique identifier (220) is detected but no tissue carrier (210) is detected to be present, as identified positions by the control unit (140, 141, 142).

17. Method according to claim 16, further comprising any of the following steps or any combination thereof:

assigning and/or linking a unique batch identification to the batch (200) based on at least one of the unique identifiers (220) of the tissue carriers (210) of the said batch (200), and linking the unique batch identification with the data acquired by the detection of the presence sensor (120) and/or the identification device (130) and/or of the identification of the control unit (140, 141, 142) and/or of any information derived therefrom and storing these linked data as batch information on a storage unit (161) of the control unit (140, 141, 142);

quantifying by the control unit (140, 141, 142) the number of
  tissue carriers (210) being detected to be present at the working area (110), and/or
  the presence positions, and/or
  unique identifiers (220) being detected to be present at the working area (110), and/or
  ID positions, which are positions of the working area (110), at which unique identifiers (220) of tissue carriers (210) of the batch (200) are detected, and/or
  the confirmed positions, which are positions of the working area (110), at which, respectively, exactly one unique identifier (220) of a tissue carrier (210) is detected and at which also exactly one tissue carrier (210) is detected to be present, and/or
  identified positions;

storing data acquired by the presence sensor (120) and the identification device (130), and/or any results of analysing the data (600, 600A, 600B) by the control unit (140, 141, 142) in a retrievable manner on a storage unit (161) of the control unit (140, 141, 142);

creating a report in a digital format comprising any of the acquired data and/or results of the quantification for output in a text format or in a graphic format or both;

moving the working area (110) relatively with respect to the presence sensor (120) and the identification device (130) for the purpose of detecting the presence of the tissue carriers (210) and the unique identifiers (220), respectively;

outputting data acquired by the detection of the presence sensor (120) and/or the identification device (130), and/or data acquired by the identification of the control unit (140, 141, 142), by an output unit;

providing a system according to claim 12, and sharing and cross-checking and/or comparing of the results (600, 600A, 600B) of the detection of the presence sensors (120) and/or the identification devices (130) and/or the identification of the control units (140, 141, 142) of each of the apparatuses (100, 100A, 100B), respectively, by all apparatuses (100, 100A, 100B) via a system control unit (310); and determining if there is any difference (610, 610A, 610B) between the results (600, 600A, 600B) of each of the apparatuses (100, 100A, 100B) as determined results (610, 610A, 610B) via system control unit (310) and outputting the determined results (610, 610A, 610B); and/or determining a batch identification belonging to a unique identifier (220) of a tissue carrier for retrieving related batch information via the system control unit (310).

* * * * *